United States Patent
Kemper (10) Patent No.: US 6,467,568 B1
(45) Date of Patent: Oct. 22, 2002

(54) PRACTICAL STETHOSCOPE COVER AND DISPENSER THEREFOR

(75) Inventor: Alicia Kemper, Gainesville, FL (US)

(73) Assignee: Covies, LLP, Gainesville, FL (US)

( * ) Notice: Subject to any disclaimer, the term of this patent is extended or adjusted under 35 U.S.C. 154(b) by 0 days.

(21) Appl. No.: 09/578,330

(22) Filed: May 25, 2000

(51) Int. Cl.⁷ .............................................. A61B 7/02

(52) U.S. Cl. ...................................... 181/131; 181/137

(58) Field of Search .................................. 181/131, 137

(56) References Cited

U.S. PATENT DOCUMENTS

| | | |
|---|---|---|
| 4,461,368 A | 7/1984 | Plourde |
| 4,867,265 A | 9/1989 | Wright |
| 4,867,268 A | 9/1989 | Ulert |
| 4,871,046 A | 10/1989 | Turner |
| 4,967,758 A | 11/1990 | Masciarotte |
| 4,995,473 A | 2/1991 | Packard |
| 5,269,314 A | 12/1993 | Kendall et al. |
| D344,798 S | 3/1994 | Baskin |
| 5,365,023 A | 11/1994 | Lawton |
| 5,396,894 A | 3/1995 | Eide et al. |
| 5,424,495 A | 6/1995 | Wurzburger |
| 5,428,193 A | 6/1995 | Mandiberg |
| 5,448,025 A | 9/1995 | Stark et al. |
| 5,466,898 A | 11/1995 | Gilbert et al. |
| 5,486,659 A | 1/1996 | Rosenbush |
| 5,564,431 A | 10/1996 | Seward |
| 5,587,561 A * | 12/1996 | Budayr et al. ............... 181/131 |
| 5,623,131 A | 4/1997 | Earnest |
| 5,686,706 A | 11/1997 | Wurzburger |
| 5,747,751 A | 5/1998 | Weckerle et al. |
| 5,808,244 A | 9/1998 | Knight et al. |
| 5,813,992 A | 9/1998 | Henwood |
| 5,921,941 A | 7/1999 | Longobardo et al. |
| 5,949,032 A | 9/1999 | Wurzburger |

FOREIGN PATENT DOCUMENTS

WO   WO 99/59471 A   11/1999

OTHER PUBLICATIONS

Weinstein, J.W., MD et al.; *Resistant Enterococci; A Prospective Study of Prevalence, Incidence, and Factors Associated with Colonization in University Hospital*, Infect Control Hosp Epidemiol, 1996; 17:36–41; Department of Medicine, Duke University Medical Center, Durham, North Carolina, USA.

Layton, M.C., MD et al.; *An Outbreak of Mupirocin–Resistant Staphylococcus Aureus on a Dermatotlogy Ward Associated with an Evironmental Reservoir*, Infect Control Hosp Epidemiol, 1993;14:369–375, Yale University School of Medicine, New Haven Connecticut, USA.

(List continued on next page.)

*Primary Examiner*—Khanh Dang
(74) *Attorney, Agent, or Firm*—Saliwanchik, Lloyd & Saliwanchik (57) ABSTRACT

The practical stethoscope cover of this invention in its most essential elements, comprises any form of material which acts as an effective, inexpensive and acoustically transmissive barrier means for easy application and removal from the head, or heads, of a stethoscope. The barrier means should be non-transmissive for dirt, organisms, oils, fluids and the like, all of which may carry pathogenic components. Significantly, embodiments of the stethoscope cover of this invention are easily applied by a physician, nurse or other medical practitioner to the head of a single-headed stethoscope or a double-headed stethoscope, typically in a quick, simple, easy single-handed operation. The barrier means comprising the stethoscope cover comprises folds, gathers or crimping at the marginal edges or medial portions thereof, providing flexibility, extensibility or elasticity to the cover, thus facilitating easy application and removal of the stethoscope cover from the head of the stethoscope. The folds, crimping or gathers on the marginal edges of the covers also assist in the retention of the stethoscope cover on the stethoscope head during use.

11 Claims, 9 Drawing Sheets

OTHER PUBLICATIONS

Noskin, G.A., MD et al.; *Recovery of Vanomycin–Resistant Enterococci on Fingertips and Environmental Surfaces,* Infect Control Hosp Epidemiol, 1995; 16:577–581, Northwestern Memorial Hospital, Chicago, Illinois, USA.

Smith, M.A., MPH et al., *Contaminated Stethoscopes Revisted,* Arch Intern Med 1996; Houston Texas, USA.

Cormican, M.G.M. et al., *The Microbial Flora of In–use Blood Pressure Cuffs,* Irish Journal of Science, 1991; 160:112–113, Galaway.

Wright, I.M.R. et al., *Stethoscope Contamination in the Neonatal Intesnsive Care Unit,* Journal of Hospital Infection, 1995; 29:65–68, UK.

Jones, J.S., MD et al., *Stethoscopes: A Potential of Infection?,* Annals of Emergency Medicine 1995; 26: 296–299, Michigan State University Collge of Medicine, Grand Reapids, Michigan, USA.

Winslow, E.H., RN, PhD, FAAN; *Research for Practice,* American Journal of Nursing, 1994, 56, Boulder, Colorado, USA.

Gerken, A. et al., *Infection Hazard from Stethoscopes in Hospital,* The Lancet, 1972, London.

Meyers, M.G., MD, *Longitudinal Evaluation of Neonatal Nosocomical Infections: Association of Infection with a Blood Pressure Cuff,* Pediatrics 1978, 61: 42–45, Iowa City, Iowa, USA.

Wurtz, R., MD, MPH et al., *Microbiologic Contamination and Cleaning Personal Medical Equipment,* JAMA, 1998 280: 519–520.

Strausbaugh, L.J. MD et al., *Emerging Infectious Diseases: Introduction, Infect Control Hosp Epidemiol,* 1998; 19: 354, Portland, Oregon, USA.

Brook, I., MD, MSc, *Bacterial Flora of Stethoscopes' Earpieces and Otitis Externa, Ann Otol Rhinol Laryngol,* 1997; 106: 751–752, Washington, D.C., USA.

Breathnach, A.S. et al., *Stethoscopes as Possible Vectors of Infection by Staphylococci,* BMJ, 1992, 305:1573–1574, London.

Assadian, O., MD, et al., *The Stethoscope as a Potential Source of Transmission of Bacteria,* Infect Control Hosp Epidemiol, 1998, 19: 298–299, USA.

Leprat, R. et al., *Why, When and How to Clean Stethoscopes,* The Journal of Hospital Infection, 1998, 80–82, London.

Bernard, L., MD et al., *Bacterial Contamination of Hospital Physicians' Stethoscopes,* Infect Control Hosp Epidemiol, 1999, 20: 626–628, USA.

Blydt–Hansen, T, MD. *Recovery of Respiratory Syncytial Virus from Stethoscopes by Conventional Viral Culture and Polymerase Chain Reaction,* The Pediactric Infectious Disease Journal, 1999, 18: 164–165, Lippincott Willaims & Wilkins, Baltimore, Maryland, USA.

* cited by examiner

PRACTICAL STETHOSCOPE COVER AND DISPENSER THEREFOR

BACKGROUND TO THE INVENTION

1. Field of the Invention

The present invention relates to practical stethoscope cover means and means for dispensing thereof, such that medical practitioners, at low cost and with minimal effort are enabled to minimize the chances of germ transmission via the stethoscope as a transmission means. In preferred embodiments of the invention, the stethoscope cover is dispensed in a single hand (left or right) action for covering a stethoscope cover. The stethoscope cover disclosed herein may also be applied to other medical and paramedical uses and devices, such as occluders used in ophthalmology.

2. Background Information

It appears to have been relatively widely recognized, as far back in medical science as the days of Dr. Semilweis that pathogens may be transmitted from one patient or one location to another via contact with physician's hands, instruments, clothing and the like. In order to stem infectious disease in an African hospital, Dr. Semilweis instituted the revolutionary (for the time) requirement that every physician, between each patient, had to carefully wash his or her hands. The beneficial effect was immediate and spectacular.

The general term used in medical science to describe the effect whereby potentially pathogenic organisms, including but not limited to bacteria, viruses, proteins, and the like, are unwittingly transmitted from one patient or location to another is "nosocomial infection." The means by which such organisms are transmitted are generally referred to a "fomites".

Medical science has advanced considerably since the days of Dr. Semilweis, and the need for cleanliness, and sterility of medical instrumentation has been generally accepted. However, in one particular area, there appears to be circumstantial evidence of nosocomial infection by a particular type of fomite: the stethoscope.

As is generally known and appreciated, the term "stethoscope" is generally applied to any instrument which a physician may utilize to amplify sounds produced by various portions of a patient's body. Typically, as is still generally the case, a stethoscope comprises a single head:or a dual-headed device. Typically, the single headed device, or one of the heads of the dual headed device is an enclosed, cavernous "bulb", wherein the enclosed bulb-comprises a taut diaphragm stretched across the opening of the bulb. In most dual head stethoscopes, the second head is merely a bell shaped device. To a port on each bulb is connected a tube, terminating in an earpiece, for insertion into the ear of a physician, nurse or other user of the stethoscope. The stethoscope operates by virtue of the taut diaphragm acting as an amplifying means for any sounds, vibrations and perturbations that occur at the surface to which the taut diaphragm is placed in contact. The combination of the cavernous bulb and the taut diaphragm is generally referred to as the stethoscope head. The amplified sounds travel from the stethoscope head, through the tube, and hence into the physicians' ear, whereby certain diagnoses may be made by the physician.

In the medical arts, the danger of nosocomial infection via patient-to-patient contact of the same stethoscope head, either with or without intermittent disinfection of the stethoscope head, has been relatively widely recognized. Yet, to date, there does not seem to have been adopted a generally used, practical, simple, inexpensive and effective means for prevention of the stethoscope head acting as a fomite. Study after study in the medical literature proclaims this danger and the need for an effective means of combating this problem. In addition, multiple patents have issued in the United States and elsewhere, purporting to address and solve this serious problem. Yet, as must be emphasized, here, it does not appear that any practical, effective, and cost-effective means has yet been generally adopted to limit or eliminate this problem.

In order to briefly survey efforts that have been made to date to address this problem in the United States patent literature, a brief discussion follows on several issued United States patents in which various barrier means, containers and the like have been described, in an effort to address the above-identified problems. The following discussion is provided, in addition, such that by comparison with the to-date described stethoscope barrier means, the virtues and differentiating features of the present invention may be appreciated by counterpoint. To assist in identifying these distinctions, the following brief description of the practical stethoscope cover of this invention is first provided, which description is greatly expanded upon in the section of this disclosure entitled "PREFERRED EMBODIMENTS OF THE INVENTION", and in the claims which follow.

The practical stethoscope cover of this invention in its most essential elements, comprises any form of material which acts as an effective, inexpensive and acoustically transmissive barrier means for easy application and removal from the head, or heads, of a stethoscope. The barrier means should be non-transmissive for dirt, organisms, oils and the like, all of which may carry pathogenic components. Ideally, the barrier material is also soft and temperature insulating, such that the stethoscope cover when applied to the head of a stethoscope acts as a buffer against the shock of cold metal to skin contact. Significantly, embodiments of the stethoscope cover of this invention are easily applied by a physician, nurse or other medical practitioner to the head of a single or dual head stethoscope, typically in a quick, simple, easy single-handed operation. This invention comprehends at least two principal stethoscope cover designs. A first principal design comprises a stethoscope cover which can be used for a single head stethoscope, such that the diaphragm of the stethoscope can, in a single-handed operation, be slipped into a pouch formed from a material which will prevent contamination of the stethoscope head by microorganisms residing on the skin of a patient. The pouch design involves a unitary piece of a material to form a flat bottom portion and an overlapped top portion having an overlapped envelope and sealed sides. Described herein below are various modifications, variations, and additions to this basic design, along with a dispensing means for use in combination with this first principal design. A second principal design comprises a stethoscope cover which can be used on single and dual head stethoscopes. The edges of the diaphragm of either type of stethoscope can easily be slipped under retaining folds formed in the cover, securing the cover to the stethoscope, while the remaining elongate material is drawn over the bell, in the case of a dual head device, or over the back (top) of the single head device, thereby completely covering and insulating the stethoscope head(s) from contamination. Described herein below are variations, modifications and additions to this second principal design, along with dispensing means for use in combination with this second principal design. A greater appreciation of the details, various embodiments, and practicality of the instant invention will be achieved upon review of the below provided section entitled "PREFERRED EMBODIMENTS OF THE INVENTION", the provided drawings and the appended claims.

Having generally described the stethoscope cover of this invention, the reader's attention is directed to the following United States patents in which various devices are described, with the intent of providing stethoscope covers.

U.S. Pat. No. 4, 871, 046 discloses and claims a disposable stethoscope head shield made form a unitary bottom portion and top portions which are connected to the bottom portion so as to define an envelope into which a stethoscope head may be inserted and an opening between the top portions through which the stethoscope head is introduced into the envelope. This stethoscope cover appears to be particularly suited only for single head stethoscopes and would appear to require more than a single hand for the stethoscope head to be inserted. Unlike the embodiments of the present invention, the device of the '046 patent is visually and labor intensive to mount on a stethoscope head, and application of the cover exposes the cover to the user's hands and other fomites. In addition, contamination from exposed portions of the '046 cover are easily moved to the portion of the cover placed in contact with a patient. Furthermore, the '046 device does not have an overlapped top portion to produce a top with an overlapped envelope nature. There is no description or suggestion of a permanent crease in the top portion to form a further sealed envelope portion. In addition, there is no description or suggestion of an attachment means, such as stiff or flexible rubber wings to be associated with the single headed stethoscope to assist the head in remaining securely within the pouch. Furthermore, the '046 patent device, while allegedly being useable for application on the bell portion of a dual head stethoscope, in practice, if the opening of the '046 device is large enough to allow entrance of the diaphragm portion, it appears that the cover would fall off of the bell portion. Finally, perforations on a roll of the '046 patent covers implies that the care-giver must use both hands to separate a cover from adjoined covers, and both hands are required to mount the cover. This is time consuming, labor intensive and is almost guaranteed to result in transfer of contamination from the hands or gloves of the user to the patient contact surface of the cover. Accordingly, neither of the principle designs disclosed herein are disclosed by this patent.

Design Patent No. 344, 798 discloses the design of a cover for the head of a stethoscope. The appearance of the disclosed design is quite different from the appearance of the present stethoscope covers and does not appear to disclose or suggest the overlapping top feature or the permanent seam features of either of the principal designs disclosed herein. Because this is a design patent, it is unclear how this device operates, but in appearance it is quite distinct from the appearance of the device of the present invention.

U.S. Pat. No. 5,269,314 discloses a stethoscope cover intended largely to increase a patient's comfort by preventing contact with the skin of a cold stethoscope head. The cover is made form a fabric having an elasticized hem. This stethoscope cover seems to be particularly suited for covering only a single head of a stethoscope and would appear to require more than a single hand for the stethoscope head to be inserted, thus increasing the risk of contamination. In addition, the described device does not have an overlapped top portion to produce a top with an overlapped envelope nature. There is no description or suggestion of a permanent crease in the top portion to form a further sealed means, such as stiff or flexible rubber wings to be associated with the single headed stethoscope to assist the head in remaining securely within the pouch.

U.S. Pat. Nos. 5,466,898 and 5,486,659 disclose elongated pouches into which the diaphragm and a portion of the stethoscope tubing may be inserted. Each of these patents disclose a form of catchment to retain the stethoscope head inside the bag (see FIGS. 3C and 4A–4C of the '659 patent). However, neither of these patents disclose or suggest an overlapped, top portion having an overlapped envelope nature or a permanent crease in the top which can act as a catchment means for the head, nor a fold at the mouth for ease of entry and to act as a catchment for the diaphragm. The present invention inverts material of the sleeve back into the interior of the sleeve at the mouth, with the length of the top side of the sleeve being slightly shorter than the bottom. This design allows for facile, single-handed introduction of the stethoscope head into the cover. In addition, as a visual guide, the present invention may incorporate coloration, for example in the form of a line or the like on the inwardly inverted bottom portion of the mouth. Furthermore, neither of these patents disclose or suggest a design wherein contiguous pouches may be used to protect both heads of a two-headed stethoscope.

U.S. Pat. Nos. 4,867,265; 4,461,368; 4,867,268; 5,448, 025 5,428,193; 5,424,495; 5,365,023; and 4,995,473 each disclose a stethoscope cover of one sort or another. However, none of these devices even begins to disclose or suggest the features of either of the principal designs outlined in this patent disclosure.

In U.S. Pat. No. 5,921,941 Issued Jul. 13, 1999— "Disposable Stethoscope Cover", an elastomeric stethoscope cover for tensioned application to a single head of a stethoscope was described: The stethoscope cover of this patent cannot be applied to two heads of a stethoscope at the same time, and it appears that application would require use of two hands. Additionally, an elastic range sufficient to grip the diaphragm of most stethoscopes would be insufficient to keep the cover on the bell portion of the stethoscope.

U.S. Pat. No. 5,686,706 Issued Nov. 11, 1997— "Dispensable, Disposable cover for Stethoscopes", is a continuation-in-part of U.S. Pat. No. 5,424,495, wherein a shield with an adhesive backing is applied to the head of a stethoscope. Accordingly, this patent incorporates the problems of stethoscope head fouling inherent in any adhesively applied cover, which is a problem overcome and avoided by the present invention. In addition, due to the design of the '706 patent device, acute visual attention is required to precisely place the cover on the stethoscope in order to ensure a "bull's-eye" application. If the cover is not bull's-eyed, an adhesive-fouled portion of the diaphragm is exposed to patient and other contaminant contact, resulting in unacceptably high germ loading of the stethoscope head. The accumulated high germ load is then passed from patient to patient when the cover is not mounted with precision.

In U.S. Pat. No. 5,949,032 Issued Sep. 7, 1999— "Stethoscope Cover and Covered Stethoscope", a plurality of adjoining flexible sheets of stethoscope covers in a stack. An adhesive is used to attach the covers to the stethoscope head and to retain the covers in a stack. There are various embodiments of the stethoscope cover defined in this patent, but none of these embodiments are intended for complete coverage of one or two headed stethoscope heads, as in the present invention.

In U.S. Pat. No. 5,747,751 Issued May 5, 1998—"Disposable Cover for Stethoscope Head", a purportedly "universal" stethoscope cover is disclosed in the form essentially of a sack fashioned for receiving and retaining either a single or a dual head stethoscope. The patent acknowledges a number of prior art patents and discusses the improvement of the patented device in terms of the ability to easily apply the covering to any of a wide variety of stethoscope covers. However, the patent discloses only the sack-like embodiment of a stethoscope cover, without disclosing smaller, more tightly fitting stethoscope covers for single or dual head stethoscopes, as in the present invention. In addition, the '751 patent does not appear to materially improve the ease of cover mounting, as it is awkward, time-consuming, visually intensive and requires use of both hands to place a single or dual head stethoscope in the sack.

In U.S. Pat. No. 5,564,431 Issued Oct. 15, 1996—"Flexible Stethoscope Cover, Cover Package and Dispensing System", disclosed is an essentially "condom-like" device for stethoscope heads, which is rolled over the head of the stethoscope. The "condom" is described as having a pair of circular webs joined together by a side wall web. It appears that the device is a unitary, elastomeric device which is delivered stored within a sterile pouch. A disposable dispensing means is disclosed as part of the invention, but is adapted for dispensing the condom-like device within sterile, sealed packets which have to be torn open to release the condom-like device, which must then be unfurled over the stethoscope head. Accordingly, it is apparent that multiple steps and two-handed handling of the stethoscope cover is required.

U.S. Pat. No. 5,808,244 Issued Jul. 28, 1997—"Protective Cover for a Contact Surface for a Stethoscope" discloses and claims a protective cover for electrostatic adherence to a contact surface of a stethoscope head. There is no disclosure of a cover which encloses the stethoscope head, as in the instant invention.

U.S. Pat. No. 5,623,131 Issued Apr. 22, 1997—"Protective Stethoscope Cover Having a Head Cover Connected to a Body Cover" discloses a combination stethoscope head cover and stethoscope tube cover, which may be a unitary cover or which may be separated into two elements. The patent does not disclose stand-alone stethoscope head covers which may be applied in a single-hand application procedure for either a one or two-headed stethoscope, as in the present invention.

While the above identified patents are directed to the same general problem to which the present invention is directed, it is noted that there remains a need in the art for a practical, inexpensive and effective means for preventing nosocomial infections by stethoscope fomites. There does not appear to have been a general acceptance by medical practitioners of any of the above described patented devices, and it is believed that this is in large measure due to the impracticality of having to expend time, energy, and visual focus for precise placement to mount or remove the known stethoscope covers. In some of these devices, the head of the stethoscope, including the diaphragm, becomes fouled with adhesives used to retain the known stethoscope covers on the stethoscope head. As a result, the problem of stethoscopes acting as fomites is exacerbated, due to the "tack" residue imparted to the stethoscope heads through use of the adhesive stethoscope covers.

The present invention addresses and overcomes the above-identified limitations and meets the long-felt need of a practical, effective and inexpensive stethoscope cover device for prevention of nosocomial infections transmitted through stethoscope use.

SUMMARY OF THE INVENTION

The practical stethoscope cover of this invention in its most essential elements, comprises any form of material which acts as an effective, inexpensive and acoustically transmissive barrier means for easy application and removal from the head, or heads, of a stethoscope. The barrier means should be non-transmissive for dirt, organisms, oils, fluids and the like, all of which may carry pathogenic components. Additionally, it is desirable for the stethoscope cover to be aesthetically appealing, soft, and user and manufacturing friendly. It is also desirable for the cover to act as a temperature buffer such that it buffers shock of cold metal to skin contact.

Significantly, embodiments of the stethoscope cover of this invention are easily applied by a physician, nurse or other medical practitioner or user to the head of a single-head stethoscope or a dual-head stethoscope, typically in a quick, simple, easy single-handed operation. This invention comprehends at least two principal stethoscope cover designs. A first principal design comprises a stethoscope cover which can be used for a single head stethoscope, such that the diaphragm of the stethoscope can, in a single-handed operation, be slipped into a pouch formed from a material which will prevent contamination of the stethoscope head by microorganisms residing on the skin of a patient, or contamination of a patient with pathogens on the head of the stethoscope. The pouch design involves a unitary piece of a material to form a flat bottom portion and an overlapped top portion having an overlapped envelope and sealed sides, a "puffed" mouth with at least one guide line for diaphragm insertion on the upper and/or lower lip of the cover. Described herein below are various modifications, variations, and additions to this basic design, along with a dispensing means for use in combination with this first principal design. A second principal design comprises a stethoscope cover which can be used for a single head or a dual head stethoscope, such that the stethoscope head(s) can easily be slipped into contiguous pouches formed from a material which will prevent contamination of the stethoscope head by microorganisms residing on the skin of a patient or contamination of a patient with pathogens on the head of the stethoscope. Described herein below are variations, modifications and additions to this second principal design, along with dispensing means for use in combination with this second principal design. A greater appreciation of the details, various embodiments, and practicality of the instant invention will be achieved upon review of the below provided section entitled "PREFERRED EMBODIMENTS OF THE INVENTION", the provided drawings and the appended claims.

Accordingly, it is one object of this invention to provide a novel, practical stethoscope cover.

It is a further object of this invention to provide a stethoscope cover which may be easily applied to a single headed stethoscope.

It is a further object of this invention to provide a stethoscope cover which may be easily applied to a dual-headed stethoscope.

It is a further object of this invention to provide a stethoscope cover which may be easily applied to a single or dual headed stethoscope.

It is a further object of this invention to provide means for retention of stethoscope covers on a stethoscope head without the need for two-handed application of the stethoscope cover.

Another object of this invention is to provide a means for facile dispensing of stethoscope covers.

It is a further object of this invention to provide a stethoscope cover comprising at least one crimp, gather or hinge.

Further objects and advantages of the invention will be appreciated from a review of the complete disclosure and the claims appended hereto.

DETAILED DESCRIPTION OF THE PREFERRED EMBODIMENTS

The practical stethoscope cover of this invention comprises any form of material which acts as an effective, inexpensive and acoustically transmissive barrier means for easy application and removal from the head, or heads, of a stethoscope. The barrier means should be non-transmissive for dirt, organisms, fluids, oils and the like, all of which may carry pathogenic components. Appropriate materials for the barrier means material include, but are not limited to, closely woven fabrics, non-woven fabrics, strong, resilient but flexible plastics, kevlars, paper, paper-thread or paper-fabric composites, rubber, silicone, and the like. Preferably, the barrier means repels fluids in contact with which the stethoscope head cover may come in contact. Ideally, the barrier means provides an essentially impermeable barrier to such fluids as blood, tears, semen, body oils and the like. Materials known in the art of baby diaper manufacture, women's panty liners, and the like, which utilize materials that are strong and resilient, as well as liquid impermeable, may well be applied in the manufacture of the stethoscope cover of the present invention. Ideally, the barrier means material is also transmissive for sound and vibrations, such that patient sounds and vibrations essential to the diagnostic applications to which the stethoscope is applied are minimally attenuated. Materials having such features are disclosed in the above-discussed U.S. Patents, all of which are hereby incorporated by reference for this purpose.

All embodiments of the stethoscope cover of this invention are easily applied by a physician, nurse or other medical practitioner to the head of a single-headed stethoscope or a double-headed stethoscope, typically in a quick, simple, easy single-handed operation.

As will be appreciated from the further description of this invention below, and by reference to the attached drawings, this invention comprehends at least two principal stethoscope cover designs. The first principal design comprises a stethoscope cover which can be used for a single head stethoscope, such that the diaphragm of the stethoscope can, in a single-handed operation, be slipped into a pouch formed from a material which will prevent contamination of the stethoscope head by microorganisms residing on the skin of a patient, or contamination of patient's with pathogens that might reside on the stethoscope head. The pouch design involves a unitary piece of a material to form a flat bottom portion and an overlapped top portion and sealed sides. Described herein below are various modifications, variations, and additions to this basic design, along with a dispensing means for use in combination with this first principal design. The second principal design comprises a stethoscope cover which can be used for a single or dual head stethoscope, such that (a) each head of the two-headed stethoscope can easily be covered by contiguous pouches, and (b) the diaphragm of a single head stethoscope is covered top and bottom with a material which will prevent contamination of any stethoscope head by microorganisms residing on the skin of a patient, and prevent microorganisms residing on the head of a stethoscope from contaminating a patient. Described herein below are variations, modifications and additions to this second principal design, along with dispensing means for use in combination with this second principal design.

Figure 1:
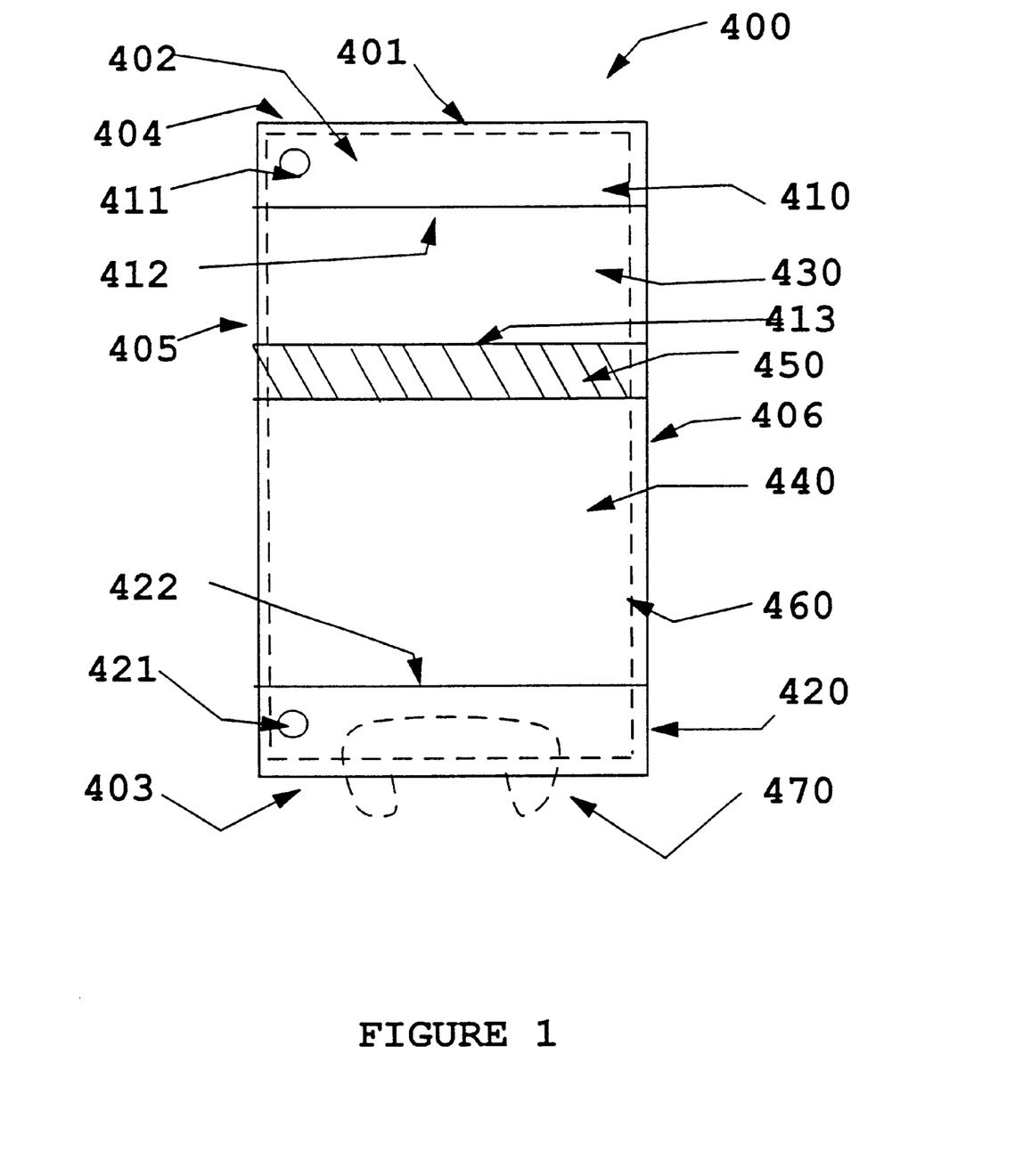
FIG. 1 shows a top view of an embodiment of the stethoscope cover of this invention which may be used to enclose a single or dual headed stethoscope.

In FIG. 1, there is shown an embodiment 400 of the stethoscope head cover of this invention, wherein fold or crimp features of the cover is in the form substantially of a single fold, crimp or hinge 450. This embodiment of the cover comprises an external (bottom) surface 401 an internal (upper) surface 402, a trailing end 403, a leading end 404, a left side 405 (viewed from the top), and a right side 406 (viewed from the top). In this embodiment, both the leading end 404 and the trailing end 403 comprise small pockets 410 and 420, respectively, formed by creating a double fold to create, upon insertion of the front edge of the rim of a stethoscope head under the edge 412 a puffed mouth, preferably having a visually detectable marking, such as a dark line or the like, as a quick visual reference, the second edge of which is edge 413, comprising a puffed mouth under which the rear of the stethoscope head rim fits. The double fold is created by folding over a portion of the bottom, external surface 401 over a portion of the internal, upper surface 402. In addition, at least one crimp or hinge 450 is formed in the cover, to form the edge 413. In this embodiment, the crimp or hinge 450 is formed by folding a portion of the upper surface body 402 of the cover over itself and affixing the fold such that the fold is permanently formed therein. This may be achieved via a thread 460 about the periphery of the cover 400. The thread may be sewn into the periphery, thereby affixing the pockets 420 and 410 and the crimp 450, if the barrier material of which the cover is formed is a material susceptible to sewing, heat sealing, welding with glue or the like. Naturally, those skilled in the art will appreciate from this disclosure that the simplest means for manufacture, for example heat sealing, is preferred for high volume production than less efficient manufacturing practices. Formed as described above, a one or two headed stethoscope is covered by inserting a rim of a stethoscope diaphragm head into the pocket 410 by slipping the rim under the opening 412, and then tilting the diaphragm so that the opposite rim of the diaphragm slips under 413 and into 450. By pulling away from a stethoscope cover dispensing means, the cover 400 is released and is attached to the stethoscope head. The trailing end 403 is then easily pulled over the top of a single or dual headed stethoscope. The cover optionally is provided with an adhesive 421 on the trailing end 403, an adhesive 411 on the leading end 404, or on both ends. The adhesive is used to retain the cover on the stethoscope head, without the need for adhesive contacting the diaphragm surface of the stethoscope head. As the trailing end 403 of the cover is pulled over the stethoscope head(s), the crimp 450 permits sufficient flexion in the body of the cover to allow the cover to be draped across the top of a single-headed stethoscope, or over both heads of a two-headed stethoscope. In the case of use of this embodiment of the stethoscope cover with a dual head stethoscope, the trailing end 403 comprises pocket 420 which has an edge 422 under which the rim of the upper stethoscope head of the dual head stethoscope may be inserted. In addition, in order to further assist in the retention of the cover on the stethoscope head, in one embodiment, the cover optionally has a tab 470 affixed to the trailing end 403 which is adhesive and which may be folded over the leading end 401 for a secure fit on the stethoscope head. The tab 470 is affixed at the perimeter of the cover and is located on the external side thereof, with the tacky or adhesive aspect thereof so disposed that upon being draped over the leading edge, it may be adhered to the leading edge. Note that the tab lies on the outside of the cover prior to use, and is useful for attaching the cover to a stethoscope or to the dispensing means prior to use of the cover. In another embodiment, an adhesive, optionally in the form of a pressure sensitive tab of adhesive, is provided at an internal location inside the cover such that when internal aspects of the stethoscope cover are brought into contact at the location of the adhesive, said internal aspects of the cover may be made to adhere to each other at that location. Optionally, where internal portions of the stethoscope cover are to come in contact with each other and be retained in contact by means of a pressure sensitive adhesive, there is provided indicia of the location of the adhesive, by means of markings, coloration or textured surfaces to assist in tactile location of said adhesive location. It will further be appreciated by those skilled in the art, based on the present disclosure, that while the embodiment of this invention shown in FIG. 1 is a substantially rectangular device, the device might just as well have rounded corners to produce a shape that is overall substantially elliptical in shape. Other variations in overall shape and size of the cover may be required, depending on the particular stethoscope dimensions required to be covered. For instance, to cover a substantial portion of the stethoscope tube, a flap the length and width of the cover is affixed to the underside, 401, and is drawn up over the lower tube area after the cover is mounted on the stethoscope.

Figure 2A:
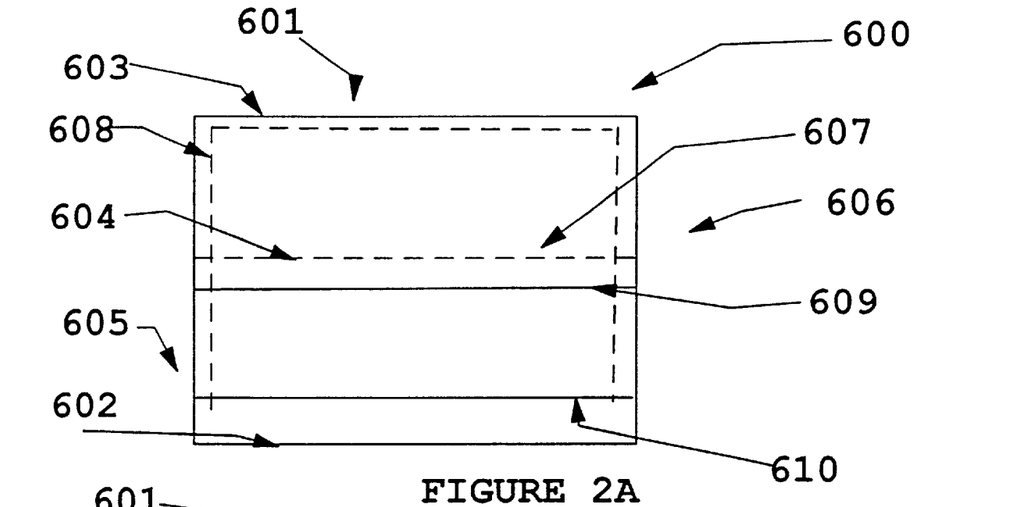
FIGS. 2(a) and 2(b) show a top view of a further embodiment of the stethoscope cover of this invention particularly suited for enclosure of a single head stethoscope.
Figure 2B:
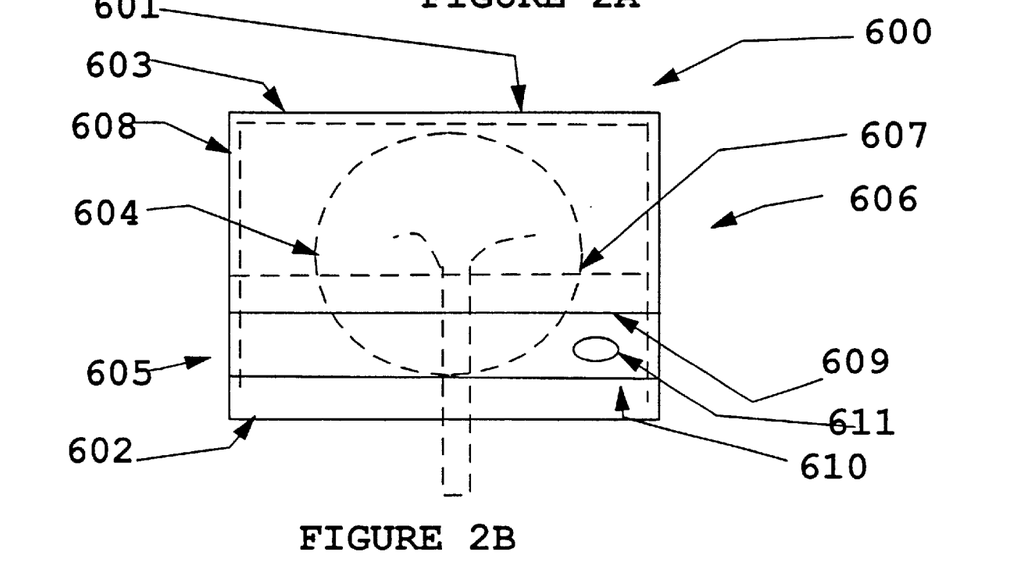

In FIG. 2, there is shown a further embodiment of the stethoscope cover of this invention, 600, most suited for a single head stethoscope. This embodiment comprises a trailing end 601, a leading end 602, an underside 603, a top side 604, a left side 605, and a right side 606. The top side 604 is folded in upon itself to form a fold line observable from the top view at 609, with an internal fold line being represented by a dashed line at 607, which is again folded internally to emerge at top edge 610. Preferably, 610 and 602 are folded inward to create a puffed mouth with guidelines for stethoscope insertion. Heat sealing, sewing, glue, thread, elastomeric material, welds, molten spots or like fixation means are shown about the periphery 608, fixing all folds and crimps in place. In use, a single head stethoscope is inserted into the pouch thus formed by sliding the stethoscope head under the top edge 610. The leading rim edge of the stethoscope head is then slid far enough into the pouch such that the trailing rim edge of the head of the single head stethoscope is made to engage the internal pouch formed by the fold created by 602 folding back on itself In this manner, the stethoscope cover 600 fits over the head of the stethoscope, and the stethoscope head is retained securely within the cover 600. Optionally, there is provided a pressure sensitive glue or low tack adhesive 611 to further secure the cover to the stethoscope. In FIG. 2B, the cover 600 is shown with a single head stethoscope inserted therein. Those skilled in the art will appreciate, based on this disclosure, that variations and modifications of this embodiment of the invention may be contemplated. Thus, for example, the precise location of the folds and the degree of overlap thereof may be varied, without departing from the essential features of this embodiment. Furthermore, in the event that there is the desire or need to cover a portion of the stethoscope tube, the length of the stethoscope cover may be extended such that the distance between the leading end 602 and trailing end 601 is sufficiently large that as much of the tubing of the stethoscope is covered as is desired. In order to retain the stethoscope cover 600 on the stethoscope, optionally adhesive or equivalent affixing means known in the art or hereafter developed are provided on the interior of 604 oriented to correspond to suitable sites on the top of the stethoscope. A baby diaper type of adhesive tab mounted on either side of the leading end of the cover is used to affix the cover to the stethoscope tube(s) or to a receiving device on the stethoscope tube(s). The releasable covering of the adhesive tab does not tear the tab off. By adhesive means or by elastic means, small "ears" of tacky material are mounted on the back of the single head stethoscope and are oriented so that they slide backward into 607 and engage with 609 after mounting. It will further be appreciated that for a dual head stethoscope, fabric heat-sealed about the proximal edge may be used. A flap of material having the same width and length of the cover may be included such that upon being pulled up the lower tube of the stethoscope may be covered.

Figure 3A:
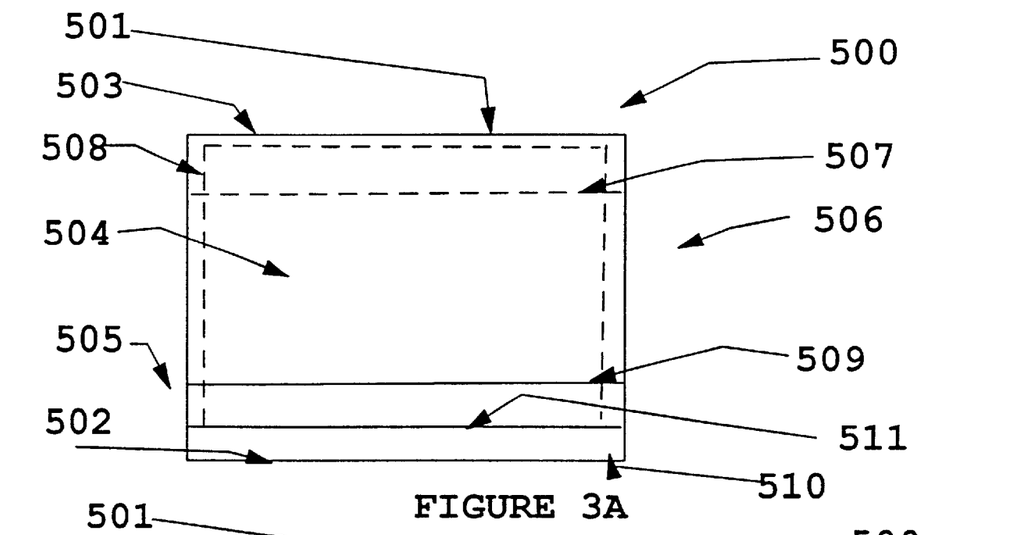
FIGS. 3(a) and 3(b) show a top view of a further embodiment of the stethoscope cover of this invention particularly suited for enclosure of a dual head stethoscope.
Figure 3B:
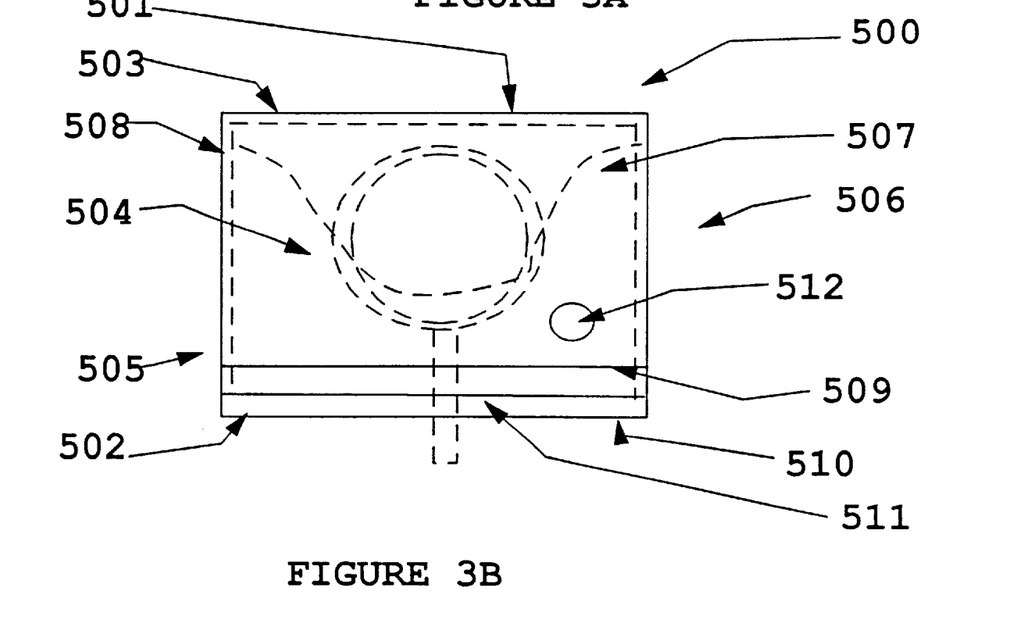

In a further embodiment of this invention, it will be appreciated that variations on the above-described embodiment of the stethoscope cover come within the scope of this invention. Thus, with reference to FIG. 3A, there is shown a further embodiment 500 of this invention most suited for a dual head stethoscope. This embodiment comprises a trailing end 501, a leading end 502, an underside 503, a top side 504, a left side 505, and a right side 506. The top side 504 is folded in upon itself to form a fold line observable from the top view at 509, with an internal fold line being represented by a dashed line at 507, which is again folded internally to emerge at top edge 510. Sewing, glue, thread, elastomeric material, welds, heat sealing, molten spots or like fixation means are shown about the periphery 508, fixing all folds and crimps in place. Top edge is spaced apart from a mouth edge 511, to form a puffed stethoscope. cover mouth into which a stethoscope head is easily inserted. Elements 510 and 511 are folded inwardly to create a puffed mouth. In use, a dual head stethoscope is inserted into the pouch thus formed by inserting the stethoscope head between the top edge 510 and the mouth edge 511, with the diaphragm side facing 510. The leading edge of the stethoscope head is then slid all the way into the pouch and 504 is pulled tightly over the bell of the stethoscope. The bell of the stethoscope is made to engage the internal pouch, the leading edge of which is defined by dotted line 507. Optionally, the bell simply functionally engages with the taut cover material. In this manner, the stethoscope cover 500 deforms to fit over both heads of the stethoscope, and the stethoscope head is retained securely within the cover 500. An internal area 512 of pressure sensitive glue or the like is optionally placed on the inside of 504 allows the cover to be used with a single head stethoscope, particularly when a matching area of glue, pressure sensitive adhesive or the like is located on the opposite internal surface of the cover to permit the cover to stay on a single head stethoscope upon bringing the two areas of adhesive in contact with each other. In FIG. 3B, the cover 500 is shown with a dual head stethoscope inserted therein. Those skilled in the art will appreciate, based on this disclosure, that variations and modifications of this embodiment of the invention may be contemplated. Thus, for example, the precise location of the folds and the degree of overlap thereof may be varied, without departing from the essential features of this embodiment. Those skilled in the art will appreciate that crimps on the top side of the cover 504 may be replaced with appropriate folds. Furthermore, in the event that there is the desire or need to cover a portion of the stethoscope tube, the length of the stethoscope cover may be extended such that the distance between the leading end 502 and trailing end 501 is sufficiently large that as much of the tubing of the stethoscope is covered as is desired.

Figure 4:
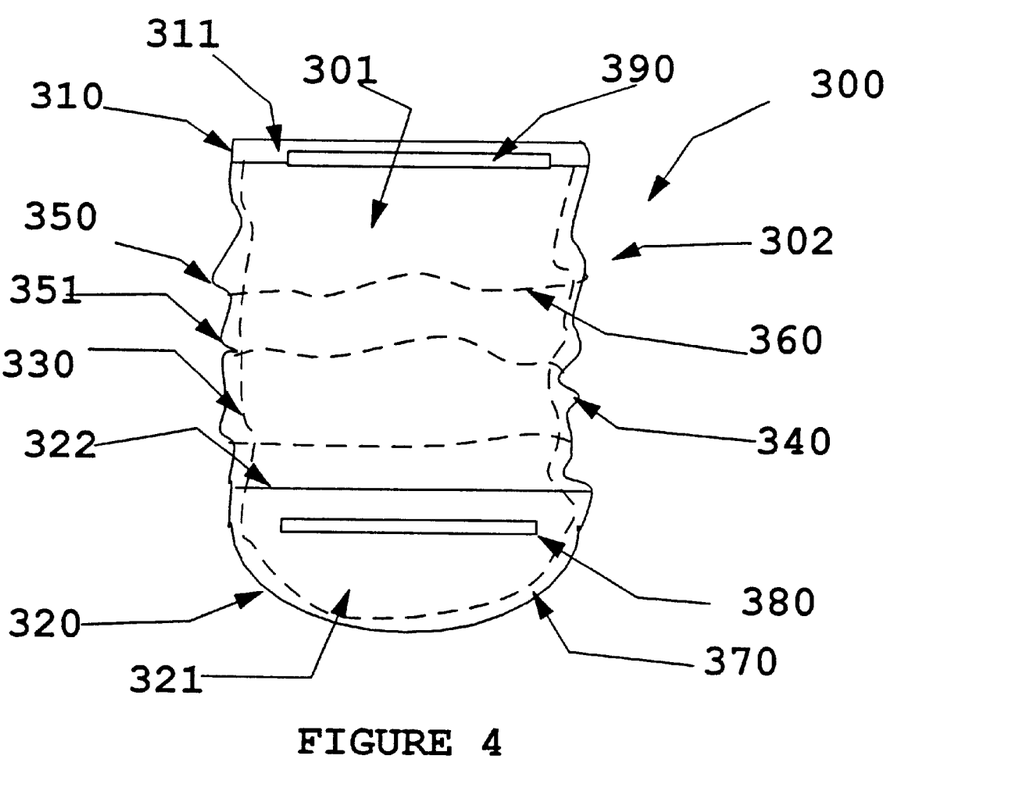
FIG. 4 shows a top view of a further embodiment of the stethoscope cover of this invention which may be used to enclose a single or dual headed stethoscope.

FIG. 4 shows an embodiment 300 of the stethoscope cover of this invention laid out extended, as it appears if laid out on a table top for viewing from the inside surface 301, which contacts the head of a stethoscope. The cover 300 also has an outside surface 302 which contacts the patient, thus insulating the actual surface of the stethoscope from contact with the patient, thereby preventing contamination of the stethoscope by the patient, or contamination of the patient by the stethoscope. Elements of the stethoscope cover 300 shown in this figure include: a leading end 320 and a trailing end 310, a first marginal side 330 and a second marginal side 340. Crimping of the margins 330 and 340 is seen 350 which produces gathers 351 and gather creases 360, when the cover 300 is not applied to a stethoscope head. Some residual creases 360 may remain once the cover 300 is extended over the head of a single head stethoscope or over the heads of a dual head stethoscope, but the creasing should not be so extensive as to interfere with sound transmission through the barrier material of the stethoscope cover 300, or to be noticeable upon contact of the external surface 302 of the cover 300 with the skin of a patient. The material is not crimped or gathered from leading end 320 over the diameter of the stethoscope head. Ideally, the cover is pulled snugly over the head(s) of the stethoscope. The crimping 350, gathers 351 and creases 360 are produced by a marginal fixation means 370 which extends about the periphery of the cover 300. The fixation means 370 may be a thread, an included elastomeric material, heat sealing or "welds" or like means. The leading end 320 preferably has a "pocket" 321 formed therein by virtue of either the bottom surface 302 being folded over onto and over a portion of the top surface 301, and being affixed thereto, or by simply affixing a matching piece of barrier material to the inside surface of the cover 300 to form the pocket 321, having a front edge 322 defining an entryway into said pocket 321 having a "puffed" mouth. In practice, the user of the cover simply hooks the rim 25 or 75 of a flat diaphragm under the front edge 322 of the cover 300, and draws the trailing end 310 over the remainder of the stethoscope head. Optionally, an opposing fold is placed in the material to catch the other side of rim 25 or 75 of a flat diaphragm, and as a result, the front edge and rear edge of the diaphragm receiving area is hooked into the cover. To assist in affixing the trailing end to the stethoscope head, a strip or spot of optionally pressure sensitive adhesive 390 is provided on the upper surface 311 of the inside of the cover 300. The upper surface 311 may be formed by simply folding over a portion of the external surface 302. In addition, optionally, a strip of adhesive 380 may be provided on the top of the "pocket" 321. In this fashion, the trailing end 310 may be releasably attached to the upper rim of a two-headed stethoscope, or to the adhesive strip 380 on the front pocket end of the cover. Optionally, the adhesive strips 380 and 390 may be covered by an easily removed paper or like covering. However, this may not be necessary, depending on the manner of storage of the clean, optionally sterile, disposable stethoscope covers. A discussion on a preferred dispensing means is provided below in which it is apparent that use of a silicone adhesive, or the like, which does not form a tight bond, but which is sufficiently tacky to keep the cover affixed to a stethoscope also permits for efficient storage and dispensing of the stethoscope cover. In FIG. 4, the front end 320 of the cover is shown as having a hemispherical shape. Naturally, based on the present disclosure, those skilled in the art will recognize that the shape of the front end 320 and the trailing end 310 is not critical. Thus, the front end 320 might just as well be square, or rectangular, and the trailing end 310 may just as well be hemispherical.

Figure 5:
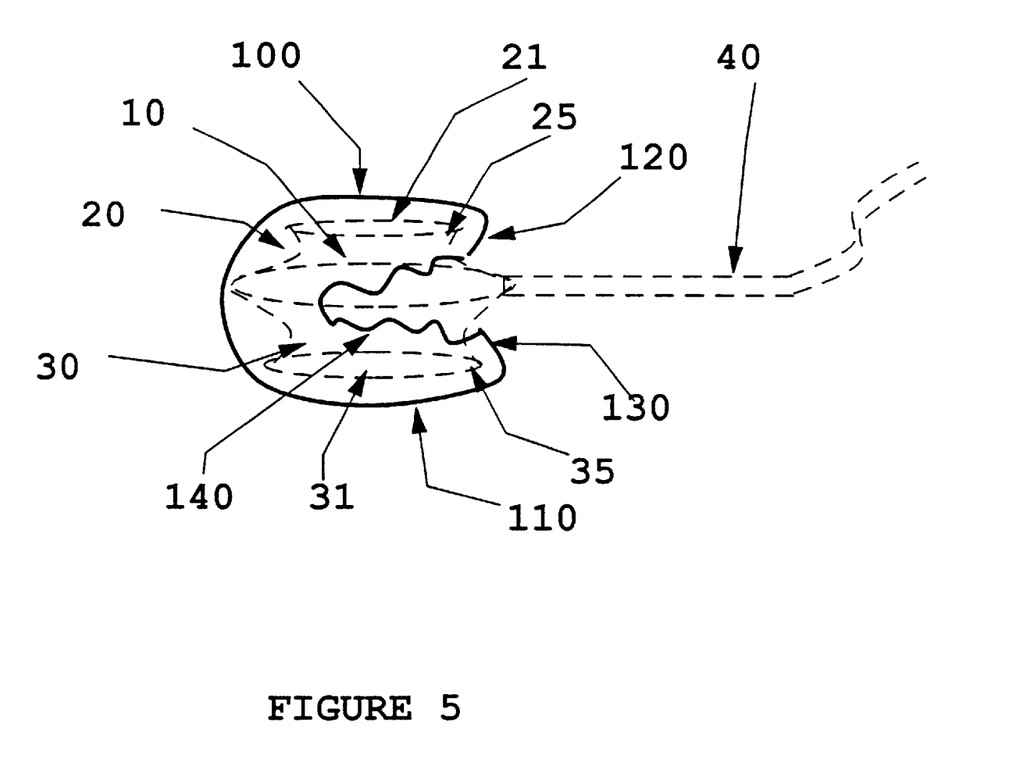
FIG. 5 shows an embodiment of the stethoscope cover of this invention wherein a side view is shown of a two-headed stethoscope enclosed within the stethoscope cover of this embodiment of this invention.

Reference is now made to FIG. 5, in which an embodiment 100 of the stethoscope cover of this invention is shown in a side view as the cover appears when applied to a two-headed stethoscope. Shown in outline is a typical dual head stethoscope 10 comprising the following typical component parts: an upper head 20, comprising an upper diaphragm 21 and an upper rim 25, a lower head 30, comprising a bell 31 and a lower rim 35; and an auditory tube 40, for transmission of sounds and vibrations to the ear of a listener (not shown). As can be seen from the sectional view of the stethoscope cover 100, the cover comprises an envelope 110 comprised of a sound-transmissive barrier means material, as described above. The envelope 110 terminates in two ends 120 and 130 which encompass the upper rim 25 of the upper head 20 and covering the upper diaphragm 21 and the lower rim 35 and the lower bell 31 of the lower head 30, respectively. Also shown is a marginal edge 140 of the stethoscope cover 100, in which the crimping or gathering of the marginal edge 140 may be clearly seen. As will be appreciated by those skilled in the art, the marginal gathering or crimping may be achieved by any known means, including, but not limited to: the simple gathering of barrier material 110 along the marginal edges and either transmitting a gathering thread therethrough with a length shorter than the length of the material from end 120 to end 130, such that the intermediate material becomes crimped; sewing of the marginal edges 140, to achieve the gathering; inclusion into a seam of such edges of an elastomeric material, such as a rubber, silicone or like material which biases the two ends 120 and 130 toward each other; heat sealing crimps into the edges of a plastic or other polymeric barrier material; inclusion of glued spot "welds" along the marginal edges; and the like. However the crimping or gathering in the marginal edges 140 is achieved, the result is that the ends 120 and 130 of the stethoscope cover 100 tightly adhere to the upper rim 25 and the lower rim 35 of the upper stethoscope head 20 and lower stethoscope head 30, respectively. Nonetheless, as will be appreciated from the following disclosure, in spite of the tight fit of the stethoscope cover 100 over the two-headed stethoscope 10, the cover 100 may be easily applied to the stethoscope head 10 in an essentially single-handed motion.

Figure 6:
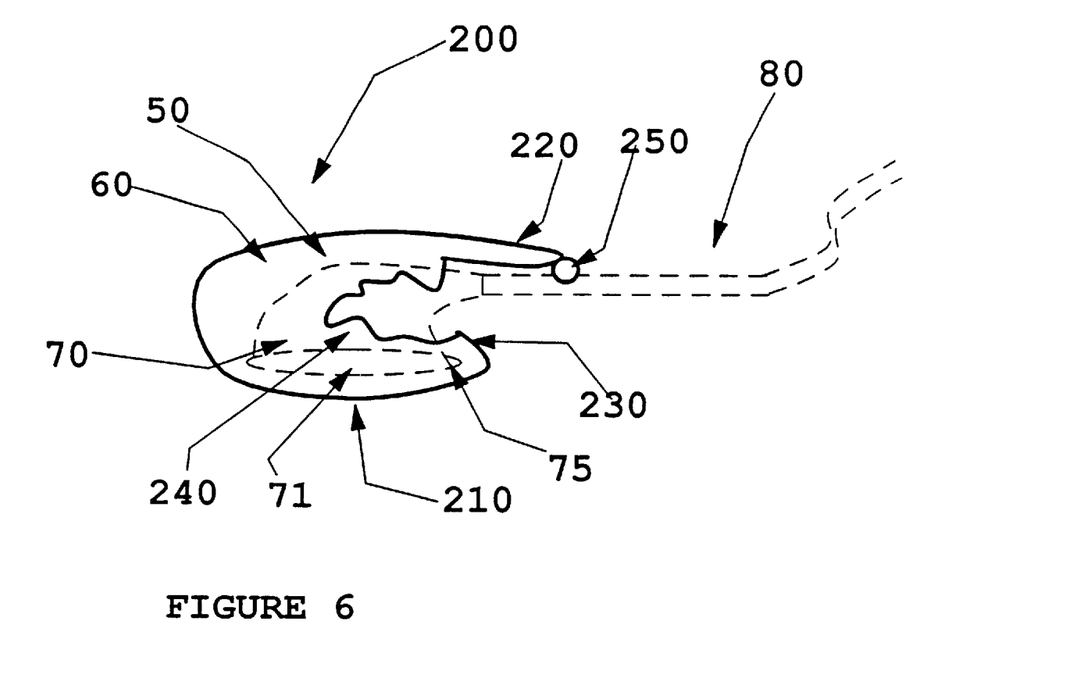
FIG. 6 shows a further embodiment of this invention enclosing a single-headed stethoscope.

In FIG. 6, there is shown a side view of variant 200 on the embodiment of the stethoscope cover 100, as it appears when applied to a single headed stethoscope 50. The single-headed stethoscope 50 is shown in outline with the following component parts: a base 60, a head 70 having a rim 75 and a diaphragm 71, and a tube 80 for transmission of sound to the user's ears (not shown). In this embodiment 200 of the stethoscope cover, the barrier material 210 is formed so as to have an extending leaf end 220 and a second end 230. The gathered margin 240 of the cover is also shown, as is a means 250 for fixing the end 220 to the stethoscope 50. The fixation means 250 may be any fixation means known in the art which may be easily applied and removed without damaging the stethoscope. For example, the fixing means 250 may be a drop of non-drying tacky material, such as a silicone, rubber, or cured glue product. In this fashion, the cover 200 may be applied to the single-headed stethoscope 50 and retained in place during use, but the cover 200 may also be easily removed after use. The fixation means 250 may alternatively be a snap means, a Velcro means, a clip, or the like, for facile fixation and removal of the cover 200. The tube or head of the stethoscope may be modified to have a complimentary snap, Velcro or like means for mating with any fixation means attached to the cover 200.

It should be appreciated that the embodiment 200 of the stethoscope cover of this invention could just as well be applied to a dual head stethoscope, as to a single head stethoscope. All that would be required-for this embodiment of the cover to be used for protection of a dual headed stethoscope would be for the extending leaf end 220 to extend sufficiently about the upper head of the dual headed stethoscope to permit fixation of the fixation means 250 to the tube 40, upper rim 25 of the upper head 20, or to the end 130 of the cover. Likewise, those skilled in the art will appreciate from the present disclosure that the embodiment 100 shown in FIG. 5 applied to a dual-headed stethoscope could just as well be used with a single-headed stethoscope. All that would be required would be for the cover 100 to have a means for fixing the end 130 or the end 120 to the other end, to the tube 80 or to the head 50 of the single headed stethoscope. It will be appreciated that for these applications, the gathering or crimping of this embodiment of the invention remains contracted when applied to a single head stethoscope, and is expanded when applied to a dual head stethoscope.

In light of the present disclosure, those skilled in the art will further appreciate that in combination with the stethoscope covers disclosed herein, various modifications, adaptations and cover retention means may be envisioned. Thus, in one embodiment, an adapter may be affixed to the head of a stethoscope which maximizes the retention in the folds of the stethoscope cover. Such an engaging means may be in the form of one or more rearwardly projecting "ears" which engage the internal folds of the cover.

In a further aspect of this invention, the stethoscope cover is provided in a dispensing means which facilitates storage and dispensing of the stethoscope cover of this invention. In this aspect of the invention, a box, carton, crate or like container is dimensioned such that a plurality of stethoscope covers of this invention are stacked one above the other. The container preferably has an aperture dimensioned to permit selection of a cover which may be releasably affixed to the rear of the container. Thread, low tack glue, crimping or like retaining means may be employed to releasably affix all or a portion of the edge of the trailing end of each stethoscope cover into the package or container. The container should also permit for close stacking of a plurality of covers while maintaining the covers in a clean, if not sterile, state. Upon insertion of stethoscope head into a selected stethoscope cover, the stethoscope may then be withdrawn from the dispenser with the stethoscope cover mounted thereon. This facilitates, for example, application of a stethoscope cover to a sterile stethoscope head, without significant opportunity for fouling or contamination of the stethoscope head. The stethoscope covers themselves may be stored sterile inside the dispenser and thus, upon being mounted on the stethoscope, provide a sterile device for use and subsequent discarding by the physician, nurse or other user of the stethoscope and stethoscope cover. Ideally, the stethoscope cover of this invention is packaged by the manufacturer in a container, preferably meeting industry standards for cleanliness and optionally sterility of like devices, comprising a perforated portion which may easily be torn away to convert said container into a dispensing means. Those skilled in the art will further appreciate from the instant disclosure that the stethoscope cover of this invention may comprise coloration, indicia instructive of the manner of application, aesthetic graphic design or coloration. In addition, it will be appreciated that the stethoscope cover may include an anti-microbial treatment. An anti-bacterial coating or the like may be applied to the cover prior to packaging to further minimize the chances of pathogen transmission.

Figure 7:
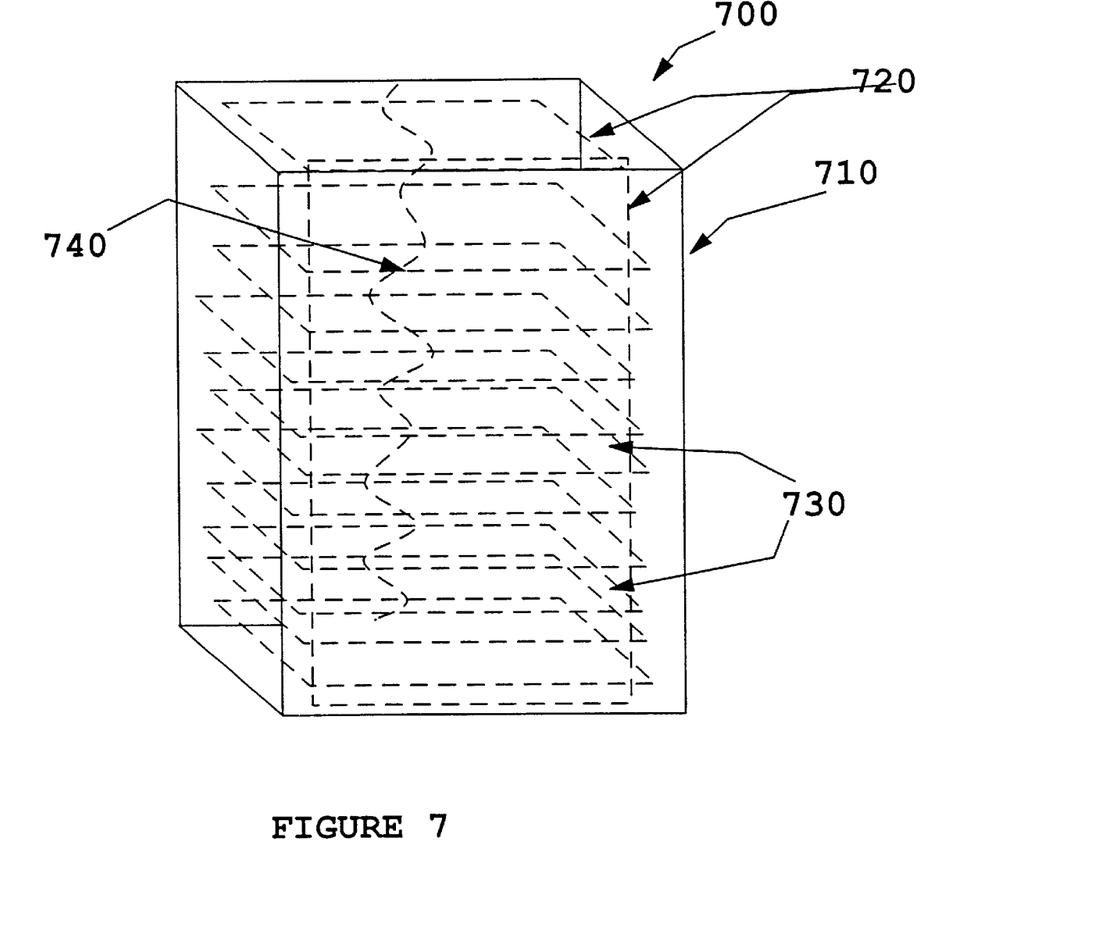
FIG. 7 shows a plurality of stethoscope covers of this invention, as stored in a dispensing means.

In connection with the packaging, shown in FIG. 7 is one embodiment of a packaging 700 device according to this invention. The packaging 700 is shown as a container or box, 710 optionally fabricated from cardboard, plastic or the like, in which is stored a plurality of stethoscope covers 730 in a clean or sterile sealed environment. Also shown is a tear section 720 which is a perforated portion of the wall of the package 710 which permits single handed access to the stethoscope covers 730. The stethoscope covers are retained in the packaging by a thread, adhesive or like means 740 affixed to the internal margin of each of the stethoscope covers or tabs affixed to the marginal edges inside the packaging 710. Upon removal of the tear section 720 a stethoscope cover is removed in a single handed motion by inserting a stethoscope head into a cover while still in the packaging 710 and then withdrawing the thus protected stethoscope head, or by first removing a stethoscope cover from the packaging 710 and then affixing the cover to a stethoscope head.

Figure 8:
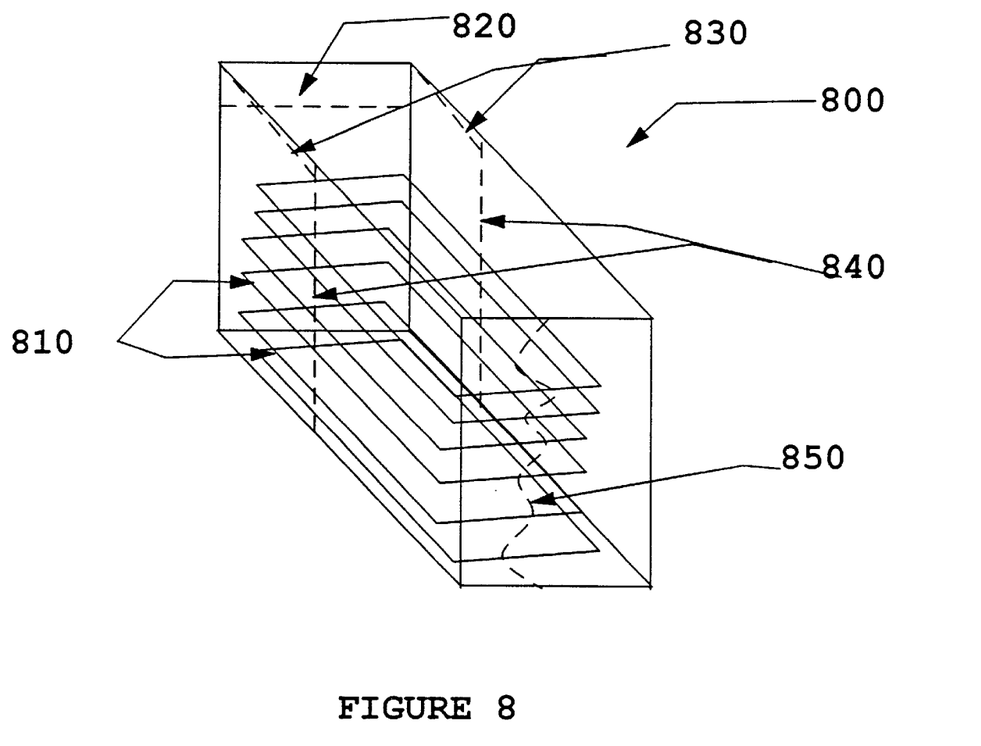
FIG. 8 shows a plurality of stethoscope covers of this invention, as stored in a dispensing means.

In FIG. 8 there is shown a dispensing device 800 for single head or a dual head stethoscope covers 810. In this embodiment of the dispensing means, a carton made from cardboard, plastic, or the like is perforated at the front end 820 along the top edges 830 and down each side 840. In this way, the front end of the carton may be removed to reveal the clean stethoscope covers 810 which may be mounted on stethoscope covers as described above, without contamination or fouling. The covers are preferably retained in the dispensing device by a retaining means such as a thread, adhesive or the like 850.

Figure 9:
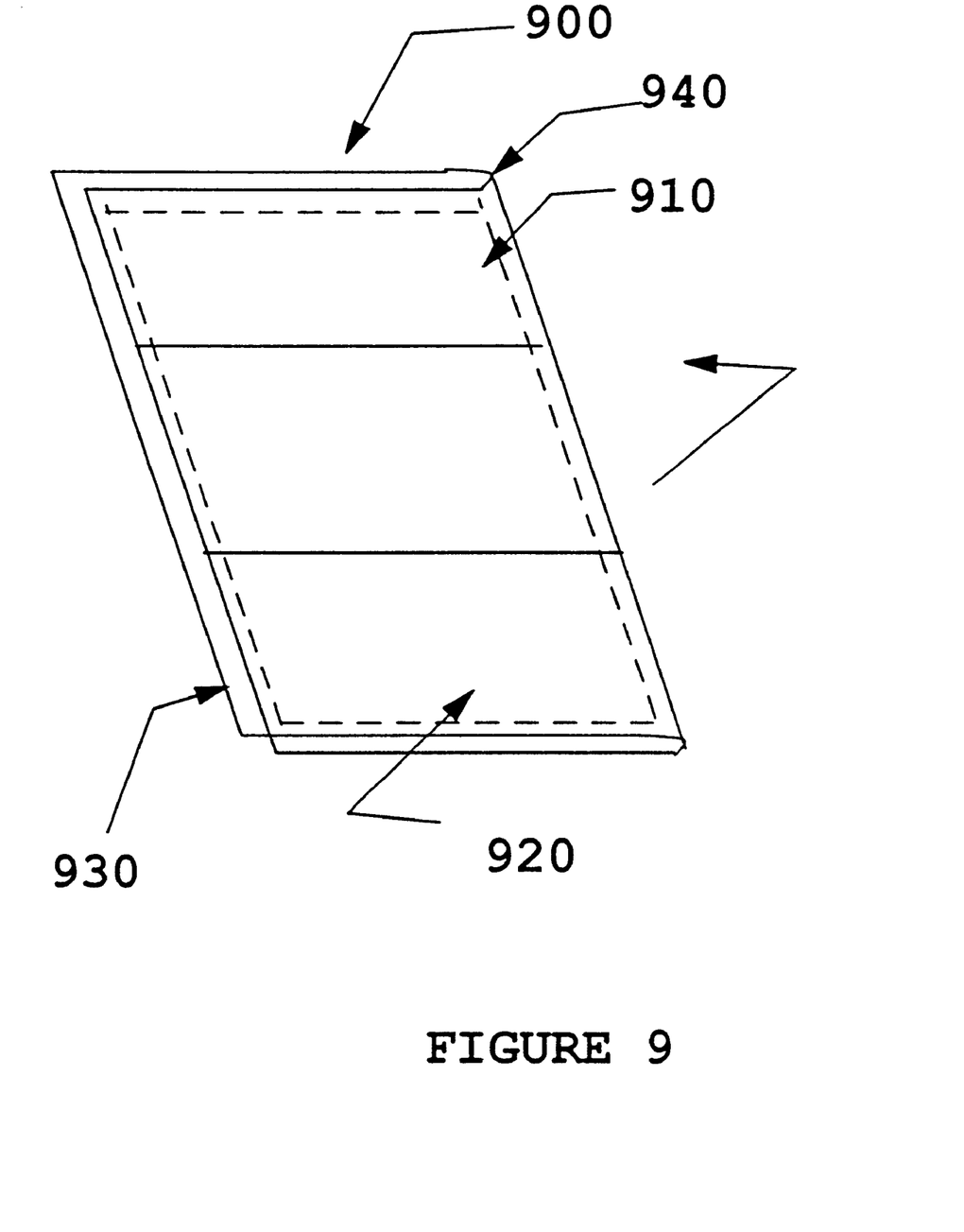
FIG. 9 shows a further embodiment of the stethoscope cover of this invention wherein an additional flap of material is provided a long one margin of the cover to assist in isolation of the stethoscope head when placed within a cover according to this invention.

In FIG. 9, there is shown yet a further aspect of the cover of this invention wherein an extra flap is provided to assist in keeping the stethoscope cover clean and clear and reducing the change of spreading germs populating the lower portion of the stethoscope tube(s). This flap, as described above, is preferably of the same width and length as the cover and is preferably affixed along an edge of the cover. The flap is oriented in the dispensing means in such a fashion that it does not interfere with efficient storage and dispensing of stethoscope covers, such as, by folding the flap below the stored covers. The embodiment 900 comprises pouches 910 and 920 for insertion of the stethoscope head (s). In addition, the embodiment 900 comprises a flap 930 which is folded around the hinge 940 in the direction of the arrow as shown. In this fashion, once the stethoscope is securely loaded into the cover, the flap, which may optionally also have an adhesive tab, tacky spot or the like, covers a portion of the stethoscope tube(s). The hinge 940 is either formed as a continuation of the materials from which the cover itself is formed, or is formed by attachment of the flap 930 to the cover along a marginal edge, by thread, heat sealant, Velcro, snaps or the like.

The packaging or dispensing means may be a wall mounted, counter mounted, tray mounted, stand-alone or small portable device. In one embodiment, the portable device is a resealable packaging, similar to, for example, a small packet of nasal tissues for pocket storage by a physician, nurse or other medical practitioner. Preferably, such a small packet of stethoscope covers contains between one and ten covers, is resealable by means of a tacky tape, clip, snap, Velcro, zipper or like closure means. In addition, such a package is preferably adapted to contain either single head stethoscope covers, dual head stethoscope covers or combinations thereof.

Having generally described the preferred embodiments of this invention, those skilled in the art will appreciate that the invention should not be interpreted as being limited to the specifics of the instant disclosure. The scope of this invention should be understood in light of the totality of the present disclosure, understanding that variations and modifications which come within the scope of the appended claims form an integral part of this invention.

What is claimed is:

1. A stethoscope cover comprising a material which acts as an effective, inexpensive and acoustically transmissive barrier means for easy application and removal from a single head stethoscope, a dual head stethoscope or both, comprising at least one fold or crimp; wherein a crimp feature of the cover is in the form substantially of a single crimp or hinge (450), and wherein said cover comprises an external (bottom) surface (401) an internal (upper) surface (402), a trailing end (403), a leading end (404), a left side (405) (viewed from the top), and a right side 406 (viewed from the top), wherein both the leading end (404) and the trailing end (403) comprise small pockets (420) and (410), respectively, formed by doubly folding over a portion of the bottom, external surface (401) over a portion of the internal, upper surface (402), and wherein at least one crimp or hinge (450) is formed in the cover by folding a portion of the body of the cover over itself.

2. The stethoscope cover according to claim 1 wherein said barrier means is non-transmissive for dirt, organisms, oils, liquids, or pathogenic organisms selected from the group consisting of closely woven fabrics, non-woven fabrics, strong, resilient but flexible plastics, kevlars, paper, paper-thread or paper-fabric composites, rubber, silicone, and laminates thereof.

3. The stethoscope cover according to claim 1 which is applicable to the head of a single-headed stethoscope, a double-headed stethoscope, or a single or double-headed stethoscope in a quick, simple, easy single-handed operation.

4. The stethoscope cover according to claim 2 wherein said barrier means comprising the stethoscope cover comprises folds, gathers or crimps at the marginal edges thereof, or at an intermediate portion thereof providing flexibility, extensibility or elasticity to the cover, thus facilitating easy application and removal of the stethoscope cover from the head of the stethoscope.

5. The stethoscope cover according to claim 4 wherein the crimping or gathers on the marginal edges of the covers assist in the retention of the stethoscope cover on the stethoscope head during use.

6. The stethoscope cover according to claim 5 wherein elastic or other elastomeric materials are included within the marginal gathers or crimping, to assist in the flexibility and retention of the cover upon application to the head of a stethoscope.

7. The stethoscope cover according to claim 1 which can be used for a single head stethoscope, such that the diaphragm of the stethoscope can, in a single-handed operation, be slipped into a pouch formed from a material which will prevent contamination of the stethoscope head by microorganisms residing on the skin of a patient.

8. The stethoscope cover according to claim 7 wherein said pouch comprises a unitary piece of a material to form a flat bottom portion and an overlapped top portion and sealed edges, thus forming an envelope for enclosing a stethoscope head.

9. The stethoscope cover according to claim 1 which can be used for a dual head stethoscope, such that each head of said dual head stethoscope can easily be slipped into contiguous pouches formed from a material which prevents contamination of either head of the stethoscope by microorganisms residing on the skin of a patient.

10. The stethoscope cover according to claim 1 wherein a one or two headed stethoscope is covered by inserting a rim of a stethoscope head into a puffed mouth of said cover defined by the pocket (410) by slipping the rim under the opening (412), tilting said edge up under edge (410) and slipping an opposite edge of said stethoscope head under a further edge (413) of the cover, thereby securing the cover to the head, optionally prior to removal of the stethoscope head from a storage or dispensing means within which said stethoscope cover is retained, drawing away from said stethoscope cover dispensing means thereby releasing said cover from said dispensing or storage means, pulling said trailing end (420) over the top of a single or dual head stethoscope, and wherein the cover optionally is provided with an adhesive (421) on the trailing end (420), an adhesive (411) on the leading end (410), or on both ends, which adhesive, if present, is used to retain the cover on the stethoscope head, without adhesive contacting the diaphragm surface of said stethoscope head, such that as the tailing end (420) of the cover is drawn over the stethoscope head(s), the crimp (450) permits the cover to lie flat over the top of a single head stethoscope or to flex and expand to allow the cover to be pulled over the second head of a dual head stethoscope.

11. The stethoscope cover according to claim 10 wherein in order to further assist in the retention of the cover on the stethoscope head or in packaging or dispensing means therefore, the cover has a tab (470) affixed top the trailing end (403) which is adhesive on one side and which may be folded over the external surface of the leading end (401), once the cover has been drawn over the second head, to ensure a secure fit on the stethoscope head.

* * * * *